(12) United States Patent
Balijepalli et al.

(10) Patent No.: US 10,138,262 B2
(45) Date of Patent: Nov. 27, 2018

(54) REACTIVE MULTI-FUNCTIONAL ADDITIVES FOR COATINGS COMPOSITIONS

(71) Applicants: Dow Global Technologies LLC, Midland, MI (US); Rohm and Haas Company, Philadelphia, PA (US)

(72) Inventors: Sudhakar Balijepalli, Midland, MI (US); Paul Doll, North Wales, PA (US); Alvin M. Maurice, Lansdale, PA (US); Jenny B. Werness, Midland, MI (US)

(73) Assignees: Dow Global Technologies LLC, Midland, MI (US); Rohm and Haas Company, Philadelphia, PA (US)

( * ) Notice: Subject to any disclaimer, the term of this patent is extended or adjusted under 35 U.S.C. 154(b) by 403 days.

(21) Appl. No.: 14/486,059

(22) Filed: Sep. 15, 2014

(65) Prior Publication Data

US 2015/0087817 A1 Mar. 26, 2015

Related U.S. Application Data

(60) Provisional application No. 61/880,511, filed on Sep. 20, 2013.

(51) Int. Cl.
| | | |
|---|---|---|
| *C08G 65/331* | (2006.01) | |
| *C07H 15/08* | (2006.01) | |
| *C08G 65/00* | (2006.01) | |
| *C08G 65/332* | (2006.01) | |
| *C08L 71/00* | (2006.01) | |

(52) U.S. Cl.
CPC ............ *C07H 15/08* (2013.01); *C08G 65/332* (2013.01); *C08G 65/3311* (2013.01); *C08G 65/3322* (2013.01); *C08L 71/00* (2013.01); *C08G 2650/26* (2013.01); *C08L 2205/00* (2013.01); *C08L 2205/02* (2013.01)

(58) Field of Classification Search
None
See application file for complete search history.

(56) References Cited

U.S. PATENT DOCUMENTS

| | | |
|---|---|---|
| 5,039,304 A | 8/1991 | Heil |
| 5,296,530 A | 3/1994 | Bors et al. |
| 5,349,026 A | 9/1994 | Emmons et al. |
| 5,426,148 A | 6/1995 | Tucker |
| 8,362,142 B2 * | 1/2013 | Stollmaier .......... C08G 18/0866 427/372.2 |
| 9,624,336 B2 * | 4/2017 | Oyaizu .............. C08G 18/4244 |
| 2005/0176874 A1 | 8/2005 | Panades et al. |
| 2007/0173602 A1 * | 7/2007 | Brinkman .......... C08F 222/1006 524/592 |
| 2011/0152439 A1 | 6/2011 | Wu et al. |
| 2013/0233739 A1 | 9/2013 | Zhao et al. |

* cited by examiner

*Primary Examiner* — Layla D Berry
*Assistant Examiner* — Bahar Craigo
(74) *Attorney, Agent, or Firm* — Karl E. Stauss; Cantor Colburn LLP

(57) ABSTRACT

A composition comprising:
(a) from 20 to 60 wt % of a saccharide component comprising from two to five sugar ring units having polymerized units of at least one alkylene oxide selected from the group consisting of ethylene oxide, propylene oxide and butylene oxide bonded to oxygen atoms on said sugar rings and at least three acetoacetyl groups bonded to terminal oxygen atoms of said polymerized units of at least one alkylene oxide; and
(b) from 40 to 80 wt % of a non-saccharide component comprising a polyol unit not containing a sugar ring and having a hydroxyl functionality from two to five; said polyol unit having polymerized units of at least one alkylene oxide selected from the group consisting of ethylene oxide, propylene oxide and butylene oxide bonded to hydroxyl oxygen atoms of the polyol and at least two acetoacetyl groups bonded to terminal oxygen atoms of said polymerized units of at least one alkylene oxide;
wherein total polymerized units of at least one alkylene oxide comprise from 20 to 80 wt % of said multifunctional additive.

3 Claims, No Drawings

REACTIVE MULTI-FUNCTIONAL ADDITIVES FOR COATINGS COMPOSITIONS

BACKGROUND OF THE INVENTION

The present invention relates to a reactive multi-functional additive composition useful for coatings formulations.

Low and zero VOC formulations of vinyl containing emulsion polymers often utilize high boiling coalescents to aid in film formation. One major drawback of such compositions is that such coalescents remain in the film longer than usual and render the films tacky. Such films also can suffer from poor block resistance. Prior art describes the use of multi-functional acetoacetates as reactive coalescents for improving film properties, for example, in U.S. Pat. No. 5,349,026. However, the materials claimed in the present application are different in composition from those of this reference. There is a need for reactive additives which impart acceptable properties to the cured paint film.

SUMMARY OF THE INVENTION

The present invention is directed to a multi-functional additive comprising:

(a) from 20 to 60 wt % of a saccharide component comprising from two to five sugar ring units having polymerized units of at least one alkylene oxide selected from the group consisting of ethylene oxide, propylene oxide and butylene oxide bonded to oxygen atoms on said sugar rings and at least three acetoacetyl groups bonded to terminal oxygen atoms of said polymerized units of at least one alkylene oxide; and (b) from 40 to 80 wt % of a non-saccharide component comprising a polyol unit not containing a sugar ring and having a hydroxyl functionality from two to five; said polyol unit having polymerized units of at least one alkylene oxide selected from the group consisting of ethylene oxide, propylene oxide and butylene oxide bonded to hydroxyl oxygen atoms of the polyol and at least two acetoacetyl groups bonded to terminal oxygen atoms of said polymerized units of at least one alkylene oxide;

wherein total polymerized units of at least one alkylene oxide comprise from 20 to 80 wt % of said multi-functional additive.

DETAILED DESCRIPTION OF THE INVENTION

All percentages herein are reported in weight percent (wt %) and all temperatures are in ° C., unless otherwise specified. Processes in which temperature is not specified are performed at room temperature (20-25° C.). Glass transition temperatures of copolymers can be readily calculated using the Fox equation (T. G. Fox, Bulletin American Physical Society, Volume 1, Issue 3, page 123 (1956)). Polymer Tg is generally very close to the minimum film formation temperature (MFFT). The MFFT may be measured directly using a temperature-gradient bar. The term "unit" refers to a compound in its reacted or polymerized form. The term "(meth)acrylate" refers to either acrylate or methacrylate; the term "(meth)acrylic" refers to acrylic or methacrylic; and the term "(meth)acrylamide" refers to acrylamide or methacrylamide.

The term "acrylic monomer" includes (meth)acrylic, maleic and itaconic acids and their $C_1$-$C_{22}$ alkyl and hydroxyalkyl esters and $C_7$-$C_{12}$ aralkyl esters; (meth)acrylamide and N-methyl- or N-dimethyl-substituted (meth)acrylamides; maleic anhydride, (meth)acrylonitrile and functional P and S containing monomers (e.g., phosphoethyl (meth)acrylate and sulfoethyl (meth)acrylate). Preferably, esters are $C_1$-$C_{12}$ alkyl and hydroxyalkyl esters, preferably $C_1$-$C_{12}$ alkyl esters, preferably $C_1$-$C_4$ alkyl esters. The term "vinyl ester monomer" includes $C_1$-$C_{22}$ alkyl esters of vinyl alcohol. The term "styrene monomer" includes styrene and styrene substituted by methyl, ethyl, hydroxymethyl or chloro groups; styrene and 4-methylstyrene (vinyltoluene) are especially preferred. The term "ethylene monomer" includes $C_1$-$C_{12}$ alkenes, preferably ethylene.

The ability of an aqueous dispersion of a vinyl addition polymer to form a film depends upon the glass transition temperature of the dispersed polymer and the temperature at which the coating is allowed to dry, as is disclosed in U.S. Pat. No. 2,795,564. The dispersed polymer is preferably obtained by emulsion polymerization of one or more monoethylenically unsaturated monomers and will have a glass transition temperature which depends, inter alia, upon the identity of the components and the proportions of the monomers in the polymer. Certain ethylenically unsaturated monomers such as, for example, methyl methacrylate, styrene, vinyl acetate, vinyl chloride, acrylonitrile, vinyl toluene, methacrylonitrile, and vinylidene chloride, produce homopolymers which have relatively high glass transition values, that is, polymers having a glass transition temperature above about 20° C. On the other hand, numerous ethylenically unsaturated monomers such as, for example, acrylic ester monomers including methyl acrylate, ethyl acrylate, butyl acrylate, 2-ethylhexyl acrylate, decyl acrylate, butyl methacrylate, isodecyl methacrylate, and hydroxyethyl acrylate; butadiene, and chloroprene produce relatively soft homopolymers, i.e., polymers having glass transition temperatures of about 20° C. or less.

By copolymerizing various hard and/or soft monomers a polymer suitable for coating or impregnating uses may be obtained having a glass transition temperature (Tg) from below about −40° C. up to about 150° C. The polymer may also incorporate other monomers capable of addition polymerization such as, for example, functional monomers as methacrylic acid, hydroxyethyl acrylate, dimethylaminoethyl methacrylate, dimethylaminopropyl methacrylamide, acetoacetoxyethyl methacrylate, sulfoethyl methacrylate, and the like; multi-ethylenically unsaturated monomers such as 1,4-butyleneglycol dimethacrylate, diallyl phthalate, divinyl benzene, and allyl methacrylate, to an extent that film formation is not unduly compromised; and the like. Coating or impregnant compositions incorporating such polymers may be made with good film-forming qualities if the Tg value of the polymer is not above the temperature at which the coating or impregnant is dried. If the Tg value or MFFT is above or near the drying temperature of the coating, then a coalescent is needed.

Preferably, the dispersed polymer with which the multi-functional additive is used has a Tg of at least 0° C., preferably at least 5° C., preferably at least 10° C., preferably at least 12° C.; preferably no greater than 40° C., preferably no greater than 35° C., preferably no greater than 30° C., preferably no greater than 28° C., preferably no greater than 26° C. Preferably, the MFFT values for the polymer are within the preceding limits Preferably, the dispersed polymer comprises from 50 to 100 wt % polymerized units of acrylic monomers based on dry polymer solids, preferably from 70 to 100 wt %, preferably from 80 to 100 wt %, preferably from 90 to 100 wt %. Preferably, the coating composition in which the multifunctional additive is used contains from 15 to 45 wt % of the dispersed polymer (as dry polymer solids), preferably from 18 to 28 wt %. Preferably, the coating composition contains from 15 to 35 wt % titanium dioxide, preferably from 18 to 28 wt %. Preferably, the coating composition contains from 30 to 70 wt % water, preferably from 40 to 60 wt %.

Preferably, the saccharide component comprises two or three sugar ring units, Preferably, the sugar ring units have a total hydroxyl functionality from 4 to 12. For clarity, this is not the hydroxyl functionality of the saccharide component, which has fewer or no hydroxyl groups, depending on the number of acetoacetyl groups. A "sugar ring unit" refers to a single sugar ring, preferably a hexose or furanose, in its reacted form, i.e., without some or all of the hydroxyl hydrogen atoms. Preferably, the saccharide component has the formula $(S)_m\{(CH_2CH(R)O)_nR^1\}_k$, where S is a single sugar ring unit, m is an integer from 2 to 5 (the term $(S)_m$ refers to m linked sugar rings, e.g., when m=2, $(S)_m$ is a disaccharide); R is hydrogen, methyl, ethyl or a mixture thereof; n is from 0.5 to 5 and represents a number average, $R^1$ is hydrogen or —$C(O)CH_2C(O)CH_3$ (acetoacetyl) and k is from 4 to 12 and represents a number average. The polymerized alkylene oxide units, —$(CH_2CH(R)O)$—, are attached by a covalent bond between the $CH_2$ and a hydroxyl oxygen on a sugar ring unit, S. k cannot be larger than the total number of hydroxyl groups on the sugar rings. Preferably, k is from 4 to 10, preferably from 4 to 8. Preferably, $R^1$ represents —$C(O)CH_2C(O)CH_3$ on from 4 to 12 of the polymerized alkylene oxide chains, preferably from 4 to 10, preferably from 4 to 8. Preferably, m is from 2 to 4, preferably 2 or 3, preferably 2. Preferably, n is from 0.5 to 5, preferably from 0.5 to 1.5. Preferred disaccharides include sucrose, lactose, maltose and lactulose Preferably R is hydrogen, methyl, or a mixture thereof; preferably methyl.

Preferably, the polyol unit of the non-saccharide component has a hydroxyl functionality from 2 to 4, preferably from 2 to 3, preferably 3. For clarity, this is not the hydroxyl functionality of the non-saccharide component, which has fewer or no hydroxyl groups, depending on the number of acetoacetyl groups. Preferred polyols having a functionality of three include, e.g., glycerol and trimethylol propane. Preferred diols include ethylene glycol, propylene glycol, butylene glycol, diethylene glycol and dipropylene glycol. Preferably, the polyol has a molecular weight no greater than 170, preferably no greater than 140; preferably no less than 62, preferably no less than 90. Preferably, the polyol is aliphatic. Preferably, the non-saccharide component has the formula $P\{(CH_2CH(R^2)O)_oR^3\}_p$, where P is the polyol unit, $R^2$ is hydrogen, methyl, ethyl or a mixture thereof; o is from 0.5 to 5 and represents a number average, $R^3$ is hydrogen or —$C(O)CH_2C(O)CH_3$ (acetoacetyl) and p (the hydroxyl functionality of the polyol, P) is from 2 to 5 and represents a number average. The polymerized alkylene oxide units, —$(CH_2CH(R^2)O)$—, are attached by a covalent bond between the $CH_2$ and a hydroxyl oxygen on a polyol unit, P. p cannot be larger than the total number of hydroxyl groups on the polyol. Preferably, p is from 2 to 4, preferably from 2 to 3, preferably 3. Preferably $R^2$ is hydrogen, methyl, or a mixture thereof; preferably methyl. Preferably, o is from 0.5 to 3, preferably from 0.5 to 1.5.

Preferably, the total polymerized units of at least one alkylene oxide (on both components) comprise at least 30 wt % of the multifunctional additive, preferably at least 40 wt %, preferably at least 45 wt %; preferably no more than 70 wt %, preferably no more than 60 wt %, preferably no more than 55 wt %. Preferably, the multi-functional additive comprises from 25 to 55 wt % of the saccharide component and from 45 to 75 wt % of the non-saccharide component, preferably from 30 to 50 wt % of the saccharide component and from 50 to 70 wt % of the non-saccharide component, preferably from 35 to 45 wt % of the saccharide component and from 55 to 65 wt % of the non-saccharide component.

Preferably, the multi-functional additive has the following structure (I)

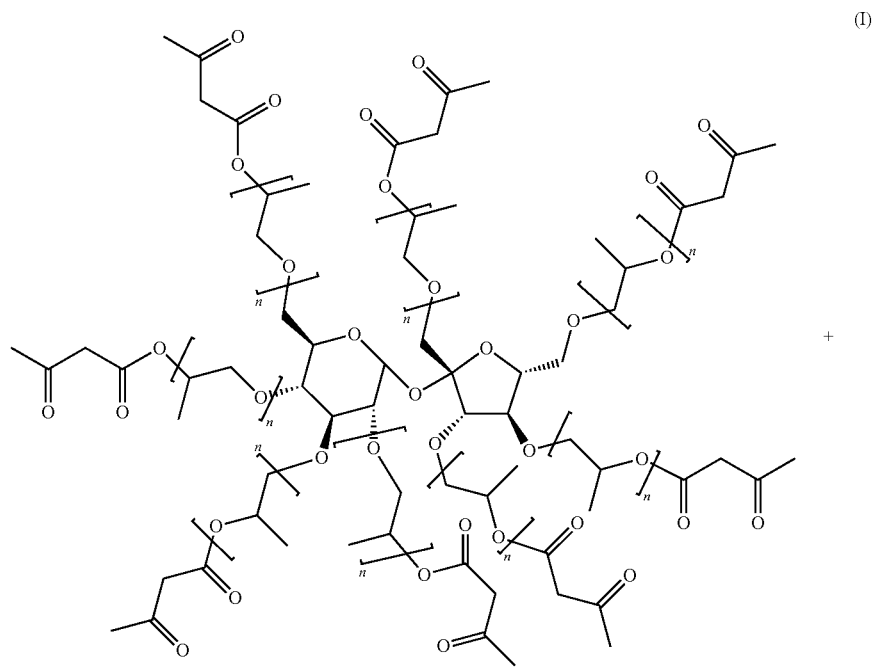

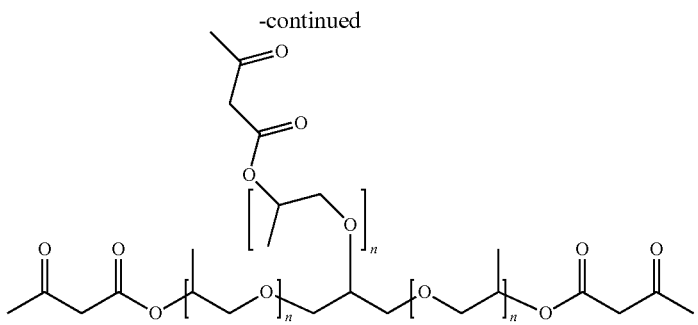

where n is from 0 to 1.5, preferably about 1. The amount of the non-saccharide component is from 58 to 66 wt %, preferably about 62 wt %. The average acetoacetyl functionality is from 4 to 5, preferably about 4.5.

Preferably, the multi-functional additive of this invention is activated through reaction of the acetoacetyl groups with ammonia or amines to produce enamine groups. The resulting enamine-functional composition is a reactive multi-functional additive. Preferably, the enamine groups are formed by reaction with an aliphatic amine, preferably a primary aliphatic amine. Preferably, the aliphatic amine is an acyclic amine Preferably, the aliphatic amine is a diamine. Preferably, the aliphatic amine is not a hydroxyl amine. Preferably, the aliphatic amine has at least one hydrogen bonded to its alpha carbon. Preferably, the molecular weight of the aliphatic amine is at least 60, preferably at least 80, preferably at least 100; preferably no more than 500, preferably no more than 400, preferably no more than 300, preferably no more than 200. Especially preferred aliphatic amines include 2-methylpentamethylenediamine and $H_2NCH(CH_3)CH_2(OCH_2CH(CH_3))_nNH_2$, where n is about 2.7 (JEFFAMINE D230). Preferably, the multi-functional additive is contacted with ammonia or the amine at a temperature from 15 to 60° C., preferably at about room temperature. Preferably, ammonia or the amine and the multi-functional additive are added to a latex paint formulation. Preferably, the ratio of the number of equivalents of amine to the number of equivalents of acetoacetate groups is from 0.8:1 to 2:1, preferably from 0.9:1 to 1.5:1, preferably from 0.98:1 to 1.02:1.

Preferably, the amount of the reactive multi-functional additive in the coating composition is from 1 to 5 wt %, preferably from 1.5 to 4 wt %. Preferably, the reactive multi-functional additive is used in combination with a low-VOC coalescent having a boiling point from 270 to 450° C., preferably from 350 to 450° C. Preferred coalescents include, e.g., OPTIFILM 400, LOXANOL EFC-200, LOXANOL EFC-300 and SOLUSOLVE 2075. Preferably, the amount of low-VOC coalescent in the coating composition, is from 0 to 15 wt % (based on polymer solids), preferably from 2 to 8 wt %, preferably from 3 to 6 wt %.

EXAMPLES

Overall Protocol:

All paints were formulated according to Table 1. The differences among the paints were; the type and amount of coalescing aid added; the presence, amount, and type of multifunctional acetoacetyl [AcAc] additives; and the type of amine reacted with the acetoacetates. These multifunctional AcAc additives are described in detail in Table 2.

TABLE 1

Formulation used to make paints with RHOPLEX AC-261-LF acrylic binder

|  | % Solids | Weight(g) |
|---|---|---|
| Grind |  |  |
| Water | 0 | 167.30 |
| Thixotropic pigment | 100 | 1.75 |
| Acrylic Dispersant | 42 | 7.91 |
| Dispersing Surfactant | 80 | 1.16 |
| Defoamer | 100 | 1.00 |
| Titanium Dioxide | 100 | 221.20 |
| Calcium Carbonate Extender | 100 | 58.21 |
| Alkaline Salt | 25 | 6.87 |
| HEC thickener in water | 4 | 2.33 |
| Grind Sub-total |  | 467.72 |
| LetDown |  |  |
| RHOPLEX ™ Binder | 50 | 453.44 |
| Defoamer | 100 | 1.53 |
| Ammonia (28%) | 28 | 0.35 |
| Coalescent | 100 | 4.53 |
| Defoamer | 100 | 4.58 |
| HUER KU Builder | 21.5 | 0.00 |
| HUER ICI Builder | 20 | 30.12 |
| Water | 0 | 99.38 |
| Totals |  | 1061.66 |

TABLE 2

Description of multifunctional AcAc additives

| Ref Name | Chemical Name | MW (g/mol) | functionality | Eq. Weight | Color |
|---|---|---|---|---|---|
| AATMP | Trimethylol Propane Triacetoacetate | 386 | 3 | 128.7 | light yellow |
| VORANOL 360 AcAc | Sucrose/Glycerine polyether polyAcAc | 1112 | 4.9 | 226.9 | light orange |

Preparation of VORANOL 360 AcAc

To a three-neck 1000 mL flask, equipped with reflux condenser, thermocouple, short-path distillation head, receiving flask, and magnetic stirrer, was added VORANOL_360 (210.4 g, 0.3 mol) and tert-butyl acetoacetate (tBAA) (284.7 g, 1.8 mol). The solution was heated to 115° C. internal temperature for 5 hours while stirring. The solution darkened from faint yellow to medium yellow as the reaction progressed, accompanied by slow distillation of tert-butanol. Aspirator vacuum (~100 mmHg) at 115° C. (for 10 minutes) followed by high vacuum at ~85° C. (for thirty minutes) were applied to remove remaining volatile tert-butanol byproduct as well as excess tBAA. The reaction was cooled to room temperature, and 305 g pure product was isolated (94% yield).

IR analysis showed that the area corresponding to the O—H stretch (~3060-3660 cm$^{-1}$) of the VORANOL 360 starting polyol (10.77 cm$^{-1}$) had decreased below detection limits in the case of VORANOL 360 AcAc.

$^1$H NMR (400 MHz, CDCl$_3$) δ 12.03, 5.89, 5.39, 5.03, 4.93, 4.05, 3.81, 3.51, 3.49, 3.38, 3.30, 2.61, 2.21, 1.90, 1.42, 1.21, 1.20, 1.19, 1.19, 1.08, 1.06.

$^{13}$C NMR (101 MHz, CDCl$_3$) δ 200.43, 166.56, 75.43, 75.40, 75.18, 75.05, 71.55, 71.46, 71.34, 71.28, 71.23, 70.90, 50.33, 50.31, 50.29, 50.25, 50.19, 29.96, 21.11, 17.20, 16.62, 16.52, 16.44

In the $^1$H NMR, the peaks at 3.38 and 2.21 are from the methylene and methyl groups of the acetoacetyl groups, respectively, and the peaks at 1.19 and 1.07 are due to the polymerized propylene oxide methyl groups. In the $^{13}$C NMR, the peaks at 200.4 and 166.6 are from the acetoacetate ketone and ester carbonyl carbons, respectively, and the peaks around 16.5 are from the polymerized propylene oxide methyl groups. Integration of the $^1$H NMR indicated a 1:1 ratio of AcAc and polymerized propylene oxide groups. The non-saccharide component is present at 62 wt %, with the remainder being the saccharide component. The product has the structure shown in formula (I) above.

After paints were made and allowed to equilibrate overnight their application properties were evaluated per:

Abrasive Scrub Resistance: was determined using an automated robotic scrub cluster that complies with ASTM-D2486 and the number of cycles is counted until cut through. 7 mil (0.18 mm) wet draw-downs of each paint tested were made on Leneta black vinyl (Form P121-10N) and then dried for 7 days in a controlled environment (75° F. (24° C.), 50% relative humidity (RH)). A minimum of eight replicates are run for each paint sample and the average values are used for analysis.

Dirt Pick-Up Resistance [DPUR]: was determined by making 7 mil wet draw-downs of each paint to be tested on uncoated aluminum panels and then leaving them for 7 days in a controlled environment (75° F. (24° C.), 50% RH). Then a slurry of red iron oxide (⅓$^{rd}$ Mapico 422 Iron Oxide Slurry in ⅔$^{rd}$ Water) was painted onto panels and allow to dry for 2 hrs. The panel was then immediately rinsed under running cold water for 30 sec while gently rubbing with a cheese cloth. The visual changes in the paints are then measured in accordance with ASTM D3719 and the Delta E values are presented below (a lower value is better).

Room Temperature Blocking Resistance [RT Block]: was determined in accordance with ASTM-D4946, where 3 mil (0.076 mm) wet draw-downs of each paint were made on Leneta white charts (Form WB) and allowed to dry 1 day in a controlled environment (75° F. (24° C.), 50% RH). Film samples were then cut into 1.5" (3.8 cm) squares and each square stacked onto another square so that the coated sides are in contact. Then a #8 rubber stopper is placed on top immediately followed by a 1000 g weight. These continue to sit for approximately 20 hrs after which the weights are removed and then the painted squares are separated by steadily pulling at the corners. The force, noise, and damage required to separate the squares are ranked 0 to 10 according the ASTM-D4946 scale where higher is better. At least 2 data points are obtained for each test paint.

Hot Blocking Resistance [Hot Block]: This test is identical to RT Blocking Resistance except that paint films are allowed to dry for 1 day and then the stacked cut squares with rubber stopper and 1000 g weight are place into a 50 C oven for 30 minutes. The squares are immediately removed and allowed to cool at (75° F. (24° C.), 50% RH) 30 minutes prior to being peel apart and ranked 0 to 10 according the ASTM-D4946 scale where higher is better. At least 2 data points are obtained for each test paint.

Materials:
LONZAMON AATMP from Lonza [AATMP]
RHOPLEX VSR-1050LOE from The Dow Chemical Co.
RHOPLEX AC-261LF from The Dow Chemical Co.
OPTIFILM-400 from Eastman Chemical (2,2-Dimethyl-1-Methylethyl-1,3 Propanediyl Bis 2 Methyl Propionate)
TEXANOL from Eastman Chemical (2,2,4-Trimethyl-1,3-pentanediol. monoisobutyrate)
Ammonium Hydroxide (29% in water) from Sigma Aldrich
AMP-95 from Angus Chemical (2-Amino-2-methyl-1-propanol)
JEFFAMINE D230 from Huntsman
DYTEK A (2-methylpentamethylenediamine) from Invista Percentages of multifunctional additive and coalescent are weight percentages based on amount of binder solids.

Data Set 1: Enamines with RHOPLEX AC-261 [JJS66381]

The acrylic emulsion RHOPLEX AC-261LF was used to formulate water based paints according to Table 1. In this series there are four control paints that were tested: One has TEXANOL as the sole coalescent to illustrate the desired values that are achieved with traditional VOC coalesced paints, and the other three have different levels of OPTIFILM as the sole coalescent to illustrate state of the art for zero-VOC paints and the negative contribution of the OPTIFILM to the paint properties.

The other four test paints in this series contained either acetoacetoxy-trimethylol-propane [AATMP] or VORANOL 360-acetoacetate [V360AcAc] at two levels. These multifunctional AcAc additives are described in detail in Table 2. All four [4] of these AcAc additive containing paints were coalesced with 4% OPTIFILM 400. The performance data for these paints is given in Table 3. All percentages for coalescents and AcAc additives in Table 3 are based on binder solids. The enamine form of each multifunctional AcAc was made by adding a stoichiometric amount of ammonium hydroxide to the binder prior to mixing in the AcAc.

TABLE 3

Performance data for coalesced paints made with AC-261LF binder
(HA = Heat Aged for 10 days at 50 C.)

| AC-261LF Paints | Coalesc. (%) | MultiFunc AcAc (%) | enamine | Gloss (60° C.) | Hot block | HA Hot block | scrubs |
|---|---|---|---|---|---|---|---|
| 1-CNTL-AC261 | TEXANOL (6%) | None (0%) | None | 32 | 6.5 | 6.5 | 601 |
| 2-CNT1-AC261 | OPTIFILM (4%) | None (0%) | None | 29 | 0.5 | 0.5 | 480 |

TABLE 3-continued

Performance data for coalesced paints made with AC-261LF binder
(HA = Heat Aged for 10 days at 50 C.)

| AC-261LF Paints | Coalesc. (%) | MultiFunc AcAc (%) | enamine | Gloss (60° C.) | Hot block | HA Hot block | scrubs |
|---|---|---|---|---|---|---|---|
| 3-CNTL-AC261 | OPTIFILM (6%) | None (0%) | None | 34 | 0 | 0 | 484 |
| 4-CNTL-AC261 | OPTIFILM (8%) | None (0%) | None | 36 | 0 | 0 | 521 |
| 5-COMP-AC261 | OPTIFILM (4%) | AATMP (2%) | $NH_3$ | 37 | 7 | 3 | 511 |
| 6-COMP-AC261 | OPTIFILM (4%) | AATMP (4%) | $NH_3$ | 38 | 7 | 0 | 586 |
| 7-EX.-AC261 | OPTIFILM (4%) | V360AcAc (2%) | $NH_3$ | 37 | 7 | 7.5 | 559 |
| 8-EX.-AC261 | OPTIFILM (4%) | V360AcAc (4%) | $NH_3$ | 39 | 7 | 7.5 | 581 |

VOC levels were <5 g/L, except for the first, which was >50 g/L

The Control with 4% OPTIFILM is slightly under-coalesced which is starting to have a negative impact on its gloss and yet it still has very poor block. It is believed that the Hot block is so poor with all the OPTIFILM control paints because it is a non-volatile coalescent meaning it does not leave that paint film even once the paint is dry; hence, the paint film does not harden and will stick to itself, i.e., poor blocking resistance. The volatile TEXANOL coalescent further illustrates this point allowing the film to have good block, but this paint cannot be classified as low VOC. All four paints with 2% and 4% of either AcAc additive had dramatic improvements in hot blocking resistance without the undesirable use of VOC contributing coalescing aids. Further only the VORANOL 360AcAc maintains the improved blocking resistance after the paints are heat aged. Data Set 2: Enamines with RHOPLEX VSR-1050 [JJS-6634]

The acrylic emulsion RHOPLEX VSR-1050LOE was used to formulate water based paints according to Table 1. As RHOPLEX VSR-1050LOE is a softer self film forming binder only 2% Coalescing aids, OPTIFILM-400 or TEXANOL, were added for control comparisons. For the test paints, 2 wt % (based on binder solids) V360AcAc was added, and an amount of the specified amine stoichiometric to the amount of acetoacetyl groups to be added were first mixed into the VSR1050 binder and then one of the AcAc's was added while continuing to mix. After 15 min of mixing the rest of the paint components in Table 1 were added one at a time while mixing. All paints had a viscosity of 96 Krebs Units+/−5 and pH=8.75+/−0.2. After equilibrating overnight the application properties of the paints were evaluated as previously described and values obtained are listed in Tables 4 -7. The paints were then heat aged at 50° C. for 10 days, removed and allowed to cool for at least 24 hours prior to new draw-downs being made, and the application properties re-evaluated. These heat aged [HA] results are also given in Tables 4-7.

TABLE 4

Scrub Resistance of original paints made with either AATMP or V360AcAc and
3 different amines as well as TEXANOL and OPTIFILM control paints. Also listed
are all of their scrub resistance values after heat aging the wet paints

| VSR1050LOE Paints | Coalescent | MultiFunc AcAc | +Amine | Scrub | HA-Scrub |
|---|---|---|---|---|---|
| 9-CNTL-VSR1050 | TEXANOL | None | None | 815 | 728 |
| 10-CNTL-VSR1050 | OPTIFILM | None | None | 757 | 602 |
| 11-COMP-VSR1050 | None | AATMP | AMP-95 | 618 | 763 |
| 12-COMP-VSR1050 | None | AATMP | JEFFAMINE D230 | 962 | 404 |
| 13-COMP-VSR1050 | None | AATMP | DYTEK A | 811 | 723 |
| 14-EXMPL-VS1050 | None | V360AcAc | AMP-95 | 670 | 644 |
| 15-EXMPL-VS1050 | None | V360AcAc | JEFFAMINE D230 | 871 | 919 |
| 16-EXMPL-VS1050 | None | V360AcAc | DYTEK A | 811 | 946 |

Use of diamines in conjunction with the multifunctional AcAc additives was found to increase the scrub resistance of the paint. These low-VOC paints were comparable or superior to the TEXANOL standard VOC control. However the known AATMP, an AcAc enamine with JEFFAMINE, was found to not be heat age stabile, while all the paints made with V360AcAc maintained their good scrub resistance after heat aging.

TABLE 5

DPUR of original paints made with either AATMP or V360AcAc and 3 different amines as well as TEXANOL and Optifilm control paints. Also listed are all of their DPUR values after heat aging the wet paints

| Paint | Coalesc. | MultiFunc AcAc | +Amine | DPUR | HA DPUR |
|---|---|---|---|---|---|
| 9-CNTL-VSR1050 | TEXANOL | None | None | 14.7 | 15.1 |
| 10-CNTL-VSR1050 | OPTIFILM | None | None | 14.5 | 13.6 |
| 11-COMP-VSR1050 | None | AATMP | AMP-95 | 13.4 | 18.9 |
| 12-COMP-VSR1050 | None | AATMP | JEFFAMINE D230 | 5.48 | 16.6 |
| 13-COMP-VSR1050 | None | AATMP | DYTEK A | 5.8 | 15.9 |
| 14-EXMPL-VS1050 | None | V360AcAc | AMP-95 | 15.6 | 12.8 |
| 15-EXMPL-VS1050 | None | V360AcAc | JEFFAMINE D230 | 8.2 | 8.3 |
| 16-EXMPL-VS1050 | None | V360AcAc | DYTEK A | 7.7 | 8.7 |

The DPUR of the paints formulated with multifunctional AcAc's and either the JEFFAMINE D230 diamine or the DYTEK A diamines were found to have DPUR superior to that of the control paints. However the DPUR of the paints made with the known AATMP significantly deteriorated upon heat aging, while the paints made with V360AcAc maintained their good DPUR after heat aging.

TABLE 6

RT Block of original paints made with either AATMP or V360AcAc and 3 different amines as well as TEXANOL and OPTIFILM control paints. Also listed are all of their RT Block values after heat aging the wet paints

| Paint | Coalesc. | MultiFunc AcAc | +Amine | RT Block | HA - RT Block |
|---|---|---|---|---|---|
| 9-CNTL-VSR1050 | Texanol | None | None | 8 | 7.5 |
| 10-CNTL-VSR1050 | Optifilm | None | None | 7.5 | 6.5 |
| 11-COMP-VSR1050 | None | AATMP | AMP-95 | 6.5 | 0 |
| 12-COMP-VSR1050 | None | AATMP | JEFFAMINE D230 | 8.5 | 0 |
| 13-COMP-VSR1050 | None | AATMP | DYTEK A | 9.5 | 3 |
| 14-EXMPL-VS1050 | None | V360AcAc | AMP-95 | 7.5 | 7 |
| 15-EXMPL-VS1050 | None | V360AcAc | JEFFAMINE D230 | 8.5 | 7.5 |
| 16-EXMPL-VS1050 | None | V360AcAc | DYTEK A | 8 | 8 |

These data clearly show large degradation of RT Block performance upon heat aging the paints made with the prior art AATMP, regardless of amine. However, all paints made with the V360AcAc additive maintained their original good RT Block property.

TABLE 7

Hot Block of original paints made with either AATMP or V360AcAc and 3 different amines as well as TEXANOL and Optifilm control paints. Also listed are all of their Hot Block values after heat aging the wet paints

| Paint | Coalesc. | MultiFunc AcAc | +Amine | Hot Block | HA - Hot Block |
|---|---|---|---|---|---|
| 9-CNTL-VSR1050 | Texanol | None | None | 7 | 7 |
| 10-CNTL-VSR1050 | Optifilm | None | None | 7 | 3.5 |
| 11-COMP-VSR1050 | None | AATMP | AMP-95 | 2.5 | 0 |
| 12-COMP-VSR1050 | None | AATMP | JEFFAMINE D230 | 7.5 | 0 |
| 13-COMP-VSR1050 | None | AATMP | DYTEK A | 7.5 | 0 |
| 14-EXMPL-VS1050 | None | V360AcAc | AMP-95 | 6.5 | 4 |
| 15-EXMPL-VS1050 | None | V360AcAc | JEFFAMINE D230 | 8 | 6.5 |
| 16-EXMPL-VS1050 | None | V360AcAc | DYTEK A | 8 | 7.5 |

These data clearly show large degradation of Hot Block performance upon heat aging the paints made with the prior art AATMP, regardless of amine. However, all paints made with the V360AcAc additive maintain their original good Hot Block property.

The invention claimed is:
1. An acrylic coating composition comprising:
(I) from 15 to 45 wt % of a dispersed polymer comprising from 80 to 100 wt % acrylic monomers;
(II) from 15 to 35 wt % titanium dioxide;
(III) from 30 to 70 wt % water; and
(IV) from 1 to 5 wt % of a reactive multi-functional additive, said reactive multi-functional additive comprising:
(i) a multi-functional additive comprising:
(a) from 30 to 50 wt % of a saccharide component having formula $(S)_m\{(CH_2CH(R)O)_n R^1\}_k$, where $R^1$ is hydrogen or —C(O)CH$_2$C(O)CH$_3$, and wherein each group of formula (CH2CH(R)O)$_n$R$^1$ is bonded to an oxygen atom; and (b) from 50 to 70 wt % of a non-saccharide component having formula P{(CH$_2$CH(R$^2$)O)$_o$R$^3$}$_p$, where R$^3$ is hydrogen or —C(O)CH$_2$C(O)CH$_3$, and wherein each group of formula (CH$_2$CH(R$^2$)O)$_n$R$^3$ is bonded to an oxygen atom;

wherein (CH$_2$CH(R)O)$_n$ and (CH$_2$CH(R$^2$)O)$_n$ collectively comprise from 30 to 70 wt % of said multifunctional additive; and wherein n is from 0.5 to 3 and represents a number average; o is from 0.5 to 3 and represents a number average; k is from 4 to 8 and represents a number average; and p is from 2 to 3 and represents a number average; and wherein (S)m is a sucrose unit and R is methyl; and wherein P is a glycerol unit and R$^2$ is methyl; and (ii) ammonia or an aliphatic amine having a molecular weight from 60 to 500, wherein the ratio of the number of equivalents of amine to the number of equivalents of acetoacetyl groups is from 0.8:1 to 2:1.

2. The composition of claim 1 in which n is from 0.5 to 1.5 and o is from 0.5 to 1.5.

3. The composition of claim 2 in which p is 3 and k is from 4 to 8.

* * * * *